(12) United States Patent
Wolter et al.

(10) Patent No.: US 8,900,180 B2
(45) Date of Patent: Dec. 2, 2014

(54) COATABLE COMPOSITIONS, COATINGS DERIVED THEREFROM AND MICROARRAYS HAVING SUCH COATINGS

(75) Inventors: James T. Wolter, Oakdale, MN (US); John K. Simons, Maplewood, MN (US); Peter R. Johnson, Eagan, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 508 days.

(21) Appl. No.: 12/092,733

(22) PCT Filed: Nov. 17, 2006

(86) PCT No.: PCT/US2006/044553
§ 371 (c)(1),
(2), (4) Date: May 6, 2008

(87) PCT Pub. No.: WO2007/061781
PCT Pub. Date: May 31, 2007

(65) Prior Publication Data
US 2008/0294116 A1    Nov. 27, 2008

Related U.S. Application Data

(60) Provisional application No. 60/753,617, filed on Dec. 23, 2005, provisional application No. 60/754,786, filed on Dec. 29, 2005, provisional application No. 60/747,618, filed on May 18, 2006.

(30) Foreign Application Priority Data

Nov. 18, 2005    (WO) ................ PCT/US2005/041858

(51) Int. Cl.
| | |
|---|---|
| *A61B 17/20* | (2006.01) |
| *A61K 9/00* | (2006.01) |
| *A61M 37/00* | (2006.01) |
| *A61K 47/26* | (2006.01) |
| *A61K 47/32* | (2006.01) |
| *A61K 47/12* | (2006.01) |

(52) U.S. Cl.
CPC ....... *A61K 9/0021* (2013.01); *A61M 2037/0023* (2013.01); *A61K 47/26* (2013.01); *A61K 47/32* (2013.01); *A61M 37/0015* (2013.01); *A61M 2037/0046* (2013.01); *A61K 47/12* (2013.01)
USPC .......................................................... 604/46

(58) Field of Classification Search
USPC ...................... 604/46–47, 173, 191, 272, 265
See application file for complete search history.

(56) References Cited

U.S. PATENT DOCUMENTS

| | | | |
|---|---|---|---|
| 3,034,507 | A | 5/1962 | McConnell et al. |
| 3,072,122 | A | 1/1963 | Rosenthal |

(Continued)

FOREIGN PATENT DOCUMENTS

| | | |
|---|---|---|
| WO | WO 96/10630 | 4/1996 |
| WO | WO 01/36037 | 5/2001 |

(Continued)

OTHER PUBLICATIONS

Gupta RK. Aluminum Compounds as Vaccine Adjuvants. Adv Drug Deliv Rev. Jul. 6, 1998;32(3):155-172.*

(Continued)

*Primary Examiner* — Kevin C Sirmons
*Assistant Examiner* — Deanna K Hall

(57) ABSTRACT

Coatable compositions and coatings derived from the coatable compositions, and microarrays comprising such coatings are described. In one aspect, the invention provides a microarray comprising: a plurality of microneedles extending from a support substrate; a coating deposited on at least one of the plurality of microneedles, the coating comprising an active agent and a biological salt. In another aspect, the invention provides a coatable composition, comprising: active agent; a biological salt; and solvent. In still another aspect, the invention provides a dried coating coated on a microneedle, the coating comprising: an active agent; and a biological salt.

8 Claims, 1 Drawing Sheet

(56) References Cited

U.S. PATENT DOCUMENTS

| | | | |
|---|---|---|---|
| 3,074,403 A | 1/1963 | Cooper et al. | |
| 3,221,740 A | 12/1965 | Rosenthal | |
| 3,678,150 A | 7/1972 | Szumski et al. | |
| 3,964,482 A * | 6/1976 | Gerstel et al. | 604/890.1 |
| 4,863,733 A * | 9/1989 | Startz et al. | 424/529 |
| 5,057,540 A | 10/1991 | Kensil et al. | |
| 5,250,023 A | 10/1993 | Lee et al. | |
| 5,437,656 A | 8/1995 | Shhikani et al. | |
| 5,457,041 A | 10/1995 | Ginaven et al. | |
| 5,611,806 A | 3/1997 | Jang | |
| 5,679,647 A | 10/1997 | Carson et al. | |
| 5,697,901 A | 12/1997 | Eriksson | |
| 5,804,566 A | 9/1998 | Carson et al. | |
| 5,879,326 A | 3/1999 | Godshall et al. | |
| 5,983,136 A | 11/1999 | Kamen | |
| 6,050,988 A | 4/2000 | Zuck | |
| 6,132,755 A | 10/2000 | Eicher et al. | |
| 6,146,632 A | 11/2000 | Momin et al. | |
| 6,256,533 B1 | 7/2001 | Yuzhakov et al. | |
| 6,299,884 B1 | 10/2001 | Van Nest et al. | |
| 6,312,612 B1 | 11/2001 | Sherman et al. | |
| 6,322,808 B1 | 11/2001 | Trautman et al. | |
| 6,331,310 B1 | 12/2001 | Roser et al. | |
| 6,334,856 B1 | 1/2002 | Allen et al. | |
| 6,352,722 B1 | 3/2002 | Blair | |
| 6,454,755 B1 | 9/2002 | Godshall | |
| 6,503,231 B1 | 1/2003 | Prausnitz et al. | |
| 6,511,463 B1 | 1/2003 | Wood et al. | |
| 6,532,386 B2 | 3/2003 | Sun et al. | |
| 6,551,622 B1 | 4/2003 | Jackson | |
| 6,591,124 B2 | 7/2003 | Sherman et al. | |
| 6,595,947 B1 | 7/2003 | Mikszta et al. | |
| 6,603,998 B1 | 8/2003 | King et al. | |
| 6,656,147 B1 | 12/2003 | Gertsek et al. | |
| 6,689,100 B2 | 2/2004 | Connelly et al. | |
| 6,713,291 B2 | 3/2004 | King et al. | |
| 6,743,211 B1 | 6/2004 | Prausnitz et al. | |
| 6,770,480 B1 | 8/2004 | Canham | |
| 6,797,276 B1 | 9/2004 | Glenn et al. | |
| 6,855,372 B2 | 2/2005 | Trautman | |
| 6,881,203 B2 | 4/2005 | Delmore et al. | |
| 6,908,453 B2 | 6/2005 | Fleming et al. | |
| 2001/0053365 A1 | 12/2001 | Friede et al. | |
| 2002/0082543 A1 | 6/2002 | Park et al. | |
| 2002/0095134 A1 | 7/2002 | Pettis et al. | |
| 2002/0102292 A1 | 8/2002 | Cormier et al. | |
| 2002/0107469 A1 * | 8/2002 | Bolan et al. | 604/6.01 |
| 2002/0128599 A1 * | 9/2002 | Cormier et al. | 604/116 |
| 2002/0138049 A1 | 9/2002 | Allen et al. | |
| 2002/0169416 A1 | 11/2002 | Gonnelli et al. | |
| 2002/0177839 A1 | 11/2002 | Cormier et al. | |
| 2002/0177858 A1 | 11/2002 | Sherman et al. | |
| 2002/0193729 A1 | 12/2002 | Cormier et al. | |
| 2002/0198509 A1 | 12/2002 | Mikszta et al. | |
| 2003/0093040 A1 | 5/2003 | Mikszta et al. | |
| 2003/0135166 A1 | 7/2003 | Gonnelli | |
| 2003/0135167 A1 | 7/2003 | Gonnelli | |
| 2003/0135172 A1 * | 7/2003 | Whitmore et al. | 604/359 |
| 2003/0135201 A1 | 7/2003 | Gonnelli | |
| 2003/0207987 A1 | 11/2003 | Leong | |
| 2004/0049150 A1 * | 3/2004 | Dalton et al. | 604/46 |
| 2004/0062813 A1 | 4/2004 | Cormier et al. | |
| 2004/0096455 A1 | 5/2004 | Maa et al. | |
| 2004/0115167 A1 | 6/2004 | Cormier et al. | |
| 2004/0176732 A1 | 9/2004 | Frazier et al. | |
| 2004/0254527 A1 * | 12/2004 | Vitello et al. | 604/82 |
| 2004/0265354 A1 | 12/2004 | Ameri et al. | |
| 2004/0265365 A1 | 12/2004 | Daddona et al. | |
| 2005/0025778 A1 | 2/2005 | Cormier et al. | |
| 2005/0049549 A1 | 3/2005 | Wong et al. | |
| 2005/0065463 A1 | 3/2005 | Tobinaga et al. | |
| 2005/0090009 A1 | 4/2005 | Cormier et al. | |
| 2005/0106226 A1 | 5/2005 | Cormier et al. | |
| 2005/0106227 A1 | 5/2005 | Zalipsky et al. | |
| 2005/0123565 A1 | 6/2005 | Subramony et al. | |
| 2005/0153873 A1 * | 7/2005 | Chan et al. | 514/2 |
| 2005/0261631 A1 | 11/2005 | Clarke et al. | |
| 2006/0253079 A1 * | 11/2006 | McDonough et al. | 604/173 |

FOREIGN PATENT DOCUMENTS

| | | | |
|---|---|---|---|
| WO | WO 03/061636 | 7/2003 | |
| WO | WO 2004/009172 | 1/2004 | |
| WO | WO 2004/060473 | 7/2004 | A61M 37/00 |
| WO | WO 2005/051455 | 6/2005 | |
| WO | WO 2005/082596 | 9/2005 | |
| WO | WO 2005/123173 | 12/2005 | |
| WO | WO 2006/055799 | 5/2006 | |

OTHER PUBLICATIONS

Daddona. Current Opinion in Drug Discovery and Development 1999 2(2);168-171.

Kaushik et al. Anesthesia Analg., 2001, 92, 502-504.

McAllister et al. Annual Review of Biomedical Engineering, 2000, 2, 289-313.

McAllister et al. Proceed. Int'l. Symp. Control Release of Bioactive Material, 26, (1999), CRS, 192-193.

Powell, M.F. And M.J. Newman (1995) Vaccine Design: The Subunit and Adjuvant Approach *Pharmaceutical Biotechnology* vol. 6, Plenum Press, NY, 949p., ISBN:0-306-44867-X. NAL call number: RS380 P53 v.6.

Powell, M.F. and M.J. Newman Vaccine Design: The Subunit and Adjuvant Approach *Pharmaceutical Biotechnology* vol. 6, Chapter 6, "Immunologic Adjuvants" pp. 69-79 Plenum Press, NY.

* cited by examiner

COATABLE COMPOSITIONS, COATINGS DERIVED THEREFROM AND MICROARRAYS HAVING SUCH COATINGS

CROSS REFERENCE TO RELATED APPLICATIONS

This application is a national stage filing under 35 U.S.C. 371 of PCT/US2006/044553, filed Nov. 17, 2006, which claims priority to Application No. PCT/US2005/041585, filed Nov. 18, 2005, Application No. 60/753,617, filed Dec. 23, 2005, Application No. 60/754,786, filed Dec. 29, 2005 and Application No. 60/747,618, filed May 18, 2006, the disclosure of which is incorporated by reference in their entirety herein.

FIELD

The present invention relates to coatable compositions and coatings derived from the coatable compositions, and to microarrays comprising such coatings.

BACKGROUND

Some therapeutic molecules can be transported through the skin. The principal barrier to the transport of molecules through the skin is the stratum corneum (the outermost layer of the skin). Devices or "microarrays" equipped with one or more microneedles have been disclosed for use in the delivery of active agents and other substances through the skin and other surfaces. In use, the microarray is pressed against the skin with sufficient force to cause the microneedles to puncture the stratum corneum and thereby create a plurality of microscopic slits through which the transdermal delivery of one or more active agents may be accomplished. Similarly, fluid sampling may be facilitated by the creation of such microscopic slits.

In delivering a therapeutic molecule or active agent through the stratum corneum, a microarray can be associated with a fluid reservoir that can temporarily retain a liquid formulation of active agent prior to its delivery through mammalian skin. In some constructions, the microneedles are hollow structures that provide a path for liquid to flow directly from the fluid reservoir through the microneedles and through the skin. In other constructions, an active agent may be coated on the outer surfaces of a microarray so that the active agent on the surfaces of the microneedles is exposed to interstitial fluids as soon as the microneedles have pierced through the stratum corneum. Once the microneedles are in contact with interstitial fluid, the coating can dissolve. The goal of such a configuration is to dissolve the active agent into the interstitial fluid so that it can enter the body to perform its therapeutic function.

However, active agents can have a strong affinity to the microneedle materials, and such an affinity can interfere with the disassociation of active agent from a microneedle surface. Although the concentration of active agent(s) in a coating can be increased to compensate for the inability to disassociate all of the active agent from the microneedles, the amount of active agent left on the microneedles of a used microarray is wasteful and can present disposal issues.

SUMMARY

The present invention provides compositions comprising active agents that can be transdermally delivered into a mammalian body from dried coatings on the outer surfaces of the microneedle(s) in a microarray. In one aspect, the invention provides a microarray comprising:

A plurality of microneedles extending from a support substrate;

A coating deposited on at least one of the plurality of microneedles, the coating comprising an active agent and a biological salt.

In another aspect, the invention provides a coatable composition, comprising:

Active agent;
A biological salt; and
Solvent.

In still another aspect, the invention provides a dried coating coated on a microneedle, the coating comprising:

An active agent; and
A biological salt.

Unless indicated herein to the contrary, words, terms or phrases will be understood as having their ordinary meaning as understood by those skilled in the art. The following definitions are applicable to the present invention.

As used herein, the terms "a," "an," "the," "at least one," and "one or more" will be understood as being interchangeable. For example, a formulation comprising "an effective amount of a pharmaceutical agent" will be understood to mean that the composition includes at least one active agent.

"Active agent" refers to one or more pharmacologically or pharmaceutically effective molecules, compounds, materials or substances producing one or more local or systemic effects in mammals, including humans. Examples of active agents include, without limitation, small molecules, polypeptides, proteins, oligonucleotides, nucleic acids, polysaccharides, drugs, vaccines or other immunologically active agents or an agent capable of triggering the production of an immunologically active agent.

"Biological salt" refers to a salt that is biologically compatible with the interstitial fluid in a mammalian body.

"Coatable composition" refers to liquid mixtures such as solutions, emulsions, dispersions and the like that include at least one active agent, solvent (e.g., water) and at least one biological salt as components thereof.

"Effective amount," when referring to the amount of active agent, refers to an amount that is sufficient to provide a local or systemic therapeutic (e.g., physiological or pharmacological) result. In a particular instance, the actual amount of active agent that is needed to provide a desired therapeutic effect will depend on a number of factors including the nature and identity of the active agent, the severity of the condition being treated, the site of delivery and the like.

"Microneedle" refers to one or more microscopic needle-like structures associated with a microarray and capable of piercing the stratum corneum to facilitate the transdermal delivery of pharmaceutical agents or the sampling of fluids through the skin.

"Microarray" refers to the medical devices described herein that includes one or more microneedles capable of piercing the stratum corneum to facilitate the transdermal delivery of therapeutic agents or the sampling of fluids through the skin.

"Vaccine" refers to conventional and/or commercially available vaccines including but not limited to the flu vaccine, Lyme disease vaccine, rabies vaccine, measles vaccine, mumps vaccine, chicken pox vaccine, small pox vaccine, hepatitis vaccine, pertussis vaccine, rubella vaccine, diphtheria vaccine, encephalitis vaccine, yellow fever vaccine, recombinant protein vaccine, DNA vaccine, polio vaccine, therapeutic cancer vaccine, herpes vaccine, pneumococcal vaccine, meningitis vaccine, whooping cough vaccine, tetanus vaccine, typhoid fever vaccine, cholera vaccine, and tuberculosis vaccine. The term "vaccine" thus includes, without limitation, antigens in the forms of proteins, polysaccarides, oligosaccarides, or weakened or killed viruses.

Those skilled in the art will more fully appreciate the features of the invention upon consideration of the remainder of the disclosure including the Detailed Description, taken together with the various Figures, and the appended claims.

BRIEF DESCRIPTION OF THE DRAWINGS

In the describing the embodiment(s) of the invention, reference is made to the various Figures in which features of the embodiments are indicated using reference numeral and wherein like reference numerals indicate like structures, and wherein.

DETAILED DESCRIPTION

The present invention provides for the delivery of active agents through the stratum corneum. In general, the described embodiments utilize coatable formulations comprising one or more active agents that may be applied to (e.g., coated on) one or more microneedles of a microarray. Once the coated formulation has dried on the microneedle(s), the microarray may be pressed against the skin of a mammal to create at least one slit and typically a plurality of slits in the stratum corneum where the dried coating will dissolve in interstitial fluids to thereby deliver the active agent.

Figure 1:
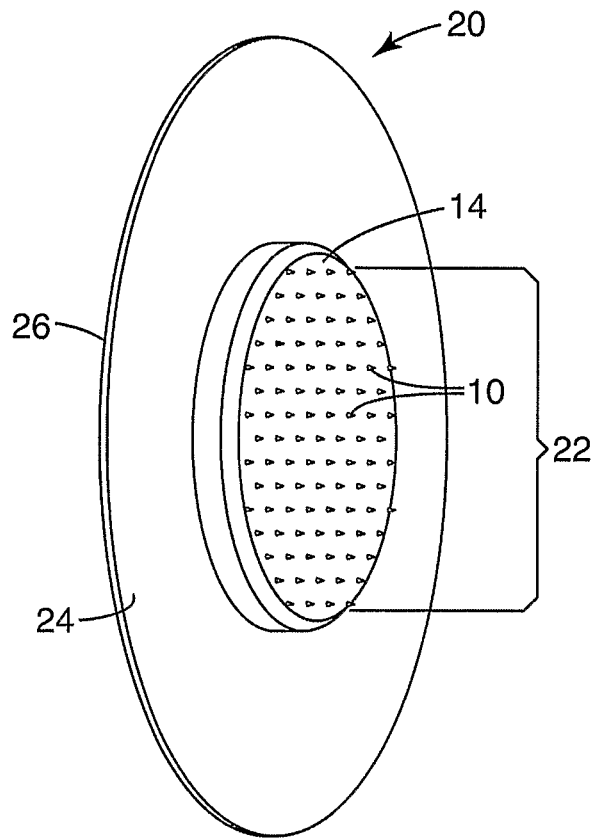
FIG. 1 is a perspective view of a patch having a microarray and suitable for use in the present invention.

Referring to the various Figures, embodiments of the invention are shown and will now be described. FIG. 1 illustrates a transdermal patch 20 in the form of a combination of a microarray 22, pressure sensitive adhesive 24 and backing 26. The microarray 22 includes a plurality of microneedles 10 protruding from a substrate surface 14. The microneedles 10 may be arranged in any desired regular or irregular pattern or they may be distributed over the substrate surface 14 randomly. The microneedles 10 are arranged in uniformly spaced rows. However, some embodiments of the invention can comprise non-uniform distributions of the microneedles, and the invention is not limited to any particular distribution or arrangement of the microneedles in the microarray. The microarray may optionally contain additional non-microstructured features, such as flanges, connectors, etc. A microarray can include a mixture of microneedles having, for example, various heights, diameters, cross-sectional shapes, and spacings between the microneedles.

In some embodiments, the height of the microneedles 10 (e.g., the distance form the substrate surface 14 and the distal end or tip of the microneedle) is between about 1 μm to about 400 μm. In some embodiments, the height of the microneedles is between about 50 μm and about 400 μm. In still other embodiments, the microneedles can have a height of between about 100 and about 400 μm. The height of the microneedle may be selected to accommodate the site on the mammalian body chosen for delivery of the active agent, namely, the stratum corneum.

Microneedles suitable for use in embodiments of the invention can be characterized as having needle or needle-like structures, or as comprising small blades or pin-like projections, all of which are capable of piercing the stratum corneum. In some embodiments, microneedles may be characterized by their aspect ratio (e.g., the ratio of the height of the microneedle to its maximum base dimension). In some embodiments of the present invention, useful microneedles can have an aspect ratio of at least about 2:1. In some embodiments, the aspect ratio may be at least about 3:1, and in still other embodiments, the aspect ratio may be at least about 5:1.

Microneedles useful in the present invention may have any of a variety of configurations. The microneedles in a single microarray may all be of the same configuration or they may comprise more than one configuration. In some embodiments of the invention, pyramidal microneedles can be used in which the microneedle has a rectangular base so that the maximum base dimension is a diagonal line connecting opposed corners across the base. In some embodiments, the microneedles may be solid, flat or may have a circular or polygonal cross section. In some embodiments, the microneedles can have straight shafts or tapered shafts and may be circular, or of some other shape (e.g., polygonal), in cross section. Microneedles suitable for use in some embodiments of the invention may have a curved blade-like configuration or they might be provided with a v-section or groove. Microneedles having other more complex shapes are also useful within the scope of the present invention to, for example, enhance adherence and fluid dynamics.

In some embodiments, useful microneedles can comprise structures like those disclosed in U.S. Pat. No. 6,881,203 B2 (Delmore et al.), issued Apr. 19, 2005. The microneedles of the '203 patent are tapered and each microneedle includes at least one channel in its outer surface. The microneedles may each have a base that is elongated in one direction, and the channel may extend from one of the ends of the elongated base to the tip of the microneedle. The channels formed along the sides of the microneedles may terminate prior to reaching the tips. Conduit structures may be provided on the surface of the base on which the microneedles are located, and the channels in the microneedles may be in fluid communication with the conduit structures. In other embodiments, the microneedles can comprise structures like those disclosed in co-pending U.S. patent application Ser. No. 10/621,620 filed on Jul. 17, 2003 entitled "Microneedle Devices and Microneedle Delivery Apparatus" which describes microneedles having a truncated tapered shape and a controlled aspect ratio.

The microneedle array for use in the present invention may comprise a plurality of microneedles. In some embodiments, there may be up to 1000 microneedles per device. In other embodiments, there may be to 500 microneedles per device. Other embodiments are also contemplated.

In embodiments of the invention, the microneedles 10 of the microarray have a patient-facing surface area of more than about 0.1 $cm^2$ and typically less than about 20 $cm^2$. In some embodiments, microneedles 10 of the microarray can have a patient-facing surface area of more than about 0.5 $cm^2$ and less than about 5 $cm^2$. In another embodiment, the surface of the microneedles 10 can comprise an area of more than about 1 percent and less than about 75 percent of the total area of the microarray surface that faces a skin surface of a patient (e.g., the combined surface area of the microneedles 10 and the substrate surface 14). In other embodiments, the surface of the microneedles 10 has an area of more than about 0.10 square inch (0.65 $cm^2$) and less than about 1 square inch (6.5 $cm^2$).

A coatable composition is used to coat the microneedles 10. The coatable composition is prepared by mixing a solvent, one or more active agents and at least one biological salt. Solvent suitable for a coatable composition can be selected from any of a variety of liquids. In embodiments of the invention, the solvent is a polar molecule that can be readily evaporated at ambient temperatures or at moderately elevated temperatures. In some embodiments, suitable solvents may be selected from liquids such as water, dimethyl sulfoxide, dimethyl formamide, ethanol, isopropyl alcohol, and mixtures of two or more of the foregoing.

In embodiments of the invention, the coatable composition is coated onto the microneedles of a microarray according to any of a variety of coating methods so that, when dried, a coating comprising active agent and biological salt remains on the distal portions (e.g., the tips) of the microneedles within the microarray. In some embodiments, the compositions are coated onto the microneedles according to the technique described in co-pending U.S. Provisional Patent Application Ser. No. 60/629,209, filed on Nov. 15, 2004, the entire disclosure of which is incorporated herein by reference thereto.

Coatable compositions useful in the invention comprise at least one biological salt. The biological salt may be, for example, an organic salt normally present in a mammalian body as a component of interstitial fluid, for example. Biological salts are selected for inclusion in the coatable compositions to be resistant to evaporation so as to become part of a dried coating that also comprises active agent. Biological salt will facilitate a relatively rapid rate of release of active agent from the dried coating. In embodiments of the invention, the rate of release of active agent in the presence of a biological salt is greater than would typically be observed for the same active agent in a coating that includes no biological salt.

In embodiments of the invention, a dried coating is formed from the coatable composition on the microneedles of a microarray. The coating comprises biological salt and active agent, and the biological salt is selected to enhance or facilitate the displacement of active agent(s) (e.g., antigens) from a substrate (e.g., a microneedle) and/or from other substances such as, for example, an adjuvant (e.g., aluminum adjuvant associated with a vaccine). Biological salt in a dried coating facilitates the rapid release of active agent into interstitial fluid, and the biological salt is chosen to have an affinity with the active agent greater than the affinity of the active agent for the microneedles or the materials from which the microneedles are made.

In some embodiments, the biological salt is an organic salt that is a carboxylated salt. In some embodiments, the biological salt is an organic salt that is a hydroxylated salt. In some embodiments, the salt is a naturally occurring component of mammalian interstitial fluid. In still other embodiments, the biological salt is not naturally occurring in mammalian interstitial fluid. Those skilled in the art will appreciate that the selection of a biological salt for inclusion in a particular coatable composition will be influenced by any of several factors such as the nature of the active agent, the material used in the microneedles of a microarray onto which a composition will be applied, the affinity of the active agent for the microprotrusion material, the affinity of the active agent for a particular biological salt, and the like.

In embodiments in which the active agent is an antigen adsorbed on an aluminum adjuvant, the biological salt may comprise one or more components normally found in interstitial fluid. In some embodiments, salts of citric acid serve as biological salts to bind a coated antigen, adjuvant, or antigen-adjuvant complex to a micro-projection. The inclusion of citric acid salts in the coatable compositions and the resulting dried coatings according to the present invention can provide a more rapid and complete dissolution and release of active agent (e.g., antigen and adjuvant) into interstitial fluid while also enhancing the coating properties of certain compositions (e.g., vaccine formulations). In aspect of the foregoing embodiment, biological salt(s) can comprise sodium and/or potassium salts of citric acid such as monosodium citrate, disodium citrate, trisodium citrate, monopotassium citrate, dipotassium citrate, tripotassium citrate and combinations of two or more of the foregoing.

One or more active agents are included in the coatable compositions and the dried coatings of the invention in amounts sufficient to deliver an effective amount of the active agent to a mammalian patient so that a desired therapeutic result can be achieved. In practice, the amount of the active agent in the coatings can vary widely depending upon the specific active agent, the site of delivery, the severity of the condition being treated, the desired therapeutic effect and the dissolution and release kinetics for delivery of the agent from the coating into skin tissues. In some embodiments, the coatable composition includes 100 parts by weight of at least one active agent, and at least 50 parts by weight of at least one biological salt.

In some embodiments, the active agent is a vaccine. In some embodiments of the invention, more than one active agent may be incorporated into the coating composition. In compositions incorporating a vaccine, the vaccine typically includes an antigen or antigenic composition capable of eliciting an immune response against a human pathogen, which antigen or antigenic composition is derived from a virus or an infectious agent that can cause disease or symptoms that can be treated with microneedle arrays of the present invention. Examples of viruses, include, but are not limited to the following DNA and RNA viruses and viral families: Arbovirus, Adenoviridae, Arenaviridae, Arterivirus, Birnaviridae, Bunyaviridae, Caliciviridae, Circoviridae, Coronaviridae, Dengue, EBV, HIV, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza A, Influenza B, and parainfluenza), Papiloma virus, Papovaviridae, Parvoviridae, Picornaviridae, Poxviridae (such as Smallpox or Vaccinia), Reoviridae (e.g., Rotavirus), Retroviridae (HTLV-I, HTLV-II, Lentivirus), *B. pertussis* (for example pertactin, pertussis toxin or derivatives thereof, filamenteous hemagglutinin, adenylate cyclase, fimbriae), *B. parapertussis* and *B. bronchiseptica* and Togaviridae (e.g., Rubivirus). Viruses falling within these families can cause a variety of diseases or symptoms, including, but not limited to: arthritis, bronchiollitis, respiratory syncytial virus, encephalitis, eye infections (e.g., conjunctivitis, keratitis), chronic fatigue syndrome, hepatitis (A, B, C, E, Chronic Active, Delta), Japanese B encephalitis, Junin, Chikungunya, Rift Valley fever, yellow fever, meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), purified or recombinant proteins thereof and viremia, polynucleotides or polypeptides, or agonists or antagonists of the invention, can be used to treat or detect any of these symptoms or diseases. In specific embodiments, microneedle arrays are used to treat: meningitis, Dengue, EBV, and/or hepatitis (e.g., hepatitis B). In an additional specific embodiment, polynucleotides, polypeptides, or agonists or antagonists of the invention are used to treat patients non-responsive to one or more other commercially available hepatitis vaccines. In a further specific embodiment, microneedles of the invention are used to treat AIDS.

Similarly, bacterial and fungal agents that can cause disease or symptoms and that can be treated with microneedle arrays of the present invention include, but not limited to, the following Gram-Negative and Gram-positive bacteria, bacterial families, and fungi: *Actinomyces* (e.g., *Norcardia*), *Acinetobacter, Cryptococcus neoformans, Aspergillus,* Bacillaceae (e.g., *Bacillus anthrasis*), *Bacteroides* (e.g., *Bacteroides fragilis*), Blastomycosis, *Bordetella, Borrelia* (e.g., *Borrelia burgdorferi*), *Brucella, Candidia, Campylobacter, Chlamydia, Clostridium* (e.g., *Clostridium botulinum, Clostridium* dificile, *Clostridium perfringens, Clostridium tetani*), *Coccidioides, Corynebacterium* (e.g., *Corynebacterium diptheriae*), *Cryptococcus, Dennatocycoses, E. coli* (e.g., Enterotoxigenic *E. coli* and Enterohemorrhagic *E. coli*), *Enterobacter* (e.g. *Enterobacter aerogenes*), Enterobacteriaceae (Klebsiella, *Salmonella* (e.g., *Salmonella typhi, Salmonella enteritidis, Salmonella typhi*), *Serratia, Yersinia, Shigella*), *Erysipelothrix, Haemophilus* (e.g., *Haemophilus influenza* type B), *Helicobacter, Legionella* (e.g., *Legionella pneumophila*), *Leptospira, Listeria* (e.g., *Listeria monocytogenes*), *Mycoplasma, Mycobacterium* (e.g., *Mycobacterium leprae* and *Mycobacterium tuberculosis*), *Vibrio* (e.g., *Vibrio cholerae*), Neisseriaceae (e.g., *Neisseria gonorrhea, Neisseria meningitidis*), Pasteurellacea, *Proteus, Pseudomonas* (e.g., *Pseudomonas aeruginosa*), Rickettsiaceae, Spirochetes (e.g., *Treponema* spp., *Leptospira* spp., *Borrelia* spp.), *Shigella* spp., *Staphylococcus* (e.g., *Staphylococcus aureus*), *Meningiococcus, Pneumococcus* and *Streptococcus* (e.g., *Streptococcus pneumoniae* and Groups A, B, and C *Streptococci*), and Ureaplasmas.

The foregoing bacterial, parasitic, and fungal families can cause diseases or symptoms, including, but not limited to: antibiotic-resistant infections, bacteremia, endocarditis, septicemia, eye infections (e.g., conjunctivitis), uveitis, tuberculosis, gingivitis, bacterial diarrhea, opportunistic infections (e.g., AIDS related infections), paronychia, prosthesis-related infections, dental caries, Reiter's Disease, respiratory tract infections, such as Whooping Cough or Emphysema, sepsis, Lyme Disease, Cat-Scratch Disease, dysentery, paratyphoid fever, food poisoning, *Legionella* disease, chronic and acute inflammation, erythema, yeast infections, typhoid, pneumonia, gonorrhea, meningitis (e.g., meningitis types A and B), chlamydia, syphilis, diphtheria, leprosy, brucellosis, peptic ulcers, anthrax, spontaneous abortions, birth defects, pneumonia, lung infections, ear infections, deafness, blindness, lethargy, malaise, vomiting, chronic diarrhea, Crohn's disease, colitis, vaginosis, sterility, pelvic inflammatory diseases, candidiasis, paratuberculosis, tuberculosis, lupus, botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections, noscomial infections.

Moreover, parasitic agents causing disease or symptoms that can be treated or prevented with microneedle arrays of the present invention include, but not limited to, the following families or class: Amebiasis, Babesiosis, Coccidiosis, Cryptosporidiosis, Dientamoebiasis, Dourine, Ectoparasitic, Giardias, Helminthiasis, Leishmaniasis, Schistisoma, Theileriasis, Toxoplasmosis, Trypanosomiasis, and *Trichomonas* and Sporozoans (e.g., *Plasmodium virax, Plasmodium falciparium, Plasmodium malariae* and *Plasmodium ovale*). These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), malaria, pregnancy complications, and toxoplasmosis.

Coatable compositions according to the present invention may include an adjuvant, although a single molecule may contain both adjuvant and antigen properties (e.g., cholera toxin). Adjuvants useful in the present invention include those known in the art—i.e., see, Vaccine Design—The Subunit and Adjuvant Approach, 1995, Pharmaceutical Biotechnology, Volume 6, Eds. Powell, M. F., and Newman, M. J., Plenum Press, New York and London, ISBN 0-306-44867-X. Adjuvants are substances used to specifically or non-specifically potentiate an antigen-specific immune response. In some embodiments, the adjuvant and the composition are mixed prior to presentation of the antigen, In other embodiments, the adjuvant and the antigen may be separately presented within a short interval of time.

Adjuvants should be capable of augmenting, enhancing, directing, or otherwise improving an immune response. Suitable adjuvants for use with the present invention include: aluminum or calcium salts (hydroxide or phosphate); aluminum phosphate gel; oil in water emulsions; particulate carriers such as liposomes; immunologically active saponin fractions (e.g. Quil A) having adjuvant activity derived from the bark of the South American tree *Quillaja Saponaria* Molina; derivatives of Quil A, for example QS21 (an HPLC purified fraction derivative of Quil A); algal glucan, β-glucan; cholera toxin B subunit, heat-shock proteins (HSPs); gamma inulin, GMDP (N-acetylglucosamine β1-4)-N-acetylmuramyl-L-alanyl-D-glutamine); GTP-GDP; Imiquimod; ImmTher® (DTP-GDP); Loxoribine, MPL®; MTP-PE; Murametide; Pleuran (β-glucan); Murapalmitine; S-28463 (4-Amino-α,α-dimethyl-1H-imidazo[4,5-c]quinoline-1-ethanol); Scalvo Peptide (IL-1β; 163-171 peptide); Theramide®; amd bacterial lipopolysaccharides such as 3D-MPL (3-O-deacylated monophosphoryl lipid A). In some embodiments, suitable adjuvants include aluminum salts, such as alum which is potassium aluminum sulfate dodecahydrate $(KAl(SO_4)_2 \cdot 12H_2O)$ and hydrolysis and hydration products of alum, such as $Al[H_2O]_6^{3+}$, $Al(OH)_2^+$, $AlO(OH)$ and $Al(OH)_3$. Further description of suitable adjuvants may be found in U.S. Pat. No. 5,057,540 (Kensil et al.), U.S. Pat. No. 6,146,632 (Momin et al.), and U.S. Pat. No. 6,299,884 (Van Nest et al.) and U.S. Patent Application Publication No. 2001/053365 (Friede et al.), the entire disclosures of which are incorporated herein by reference. Combinations of two or more of the foregoing are also contemplated.

The coatable compositions may also contain additional excipients such as viscosity modifiers, stabilizers, surfactants, pH modifiers, and other additives. Suitable additional excipients include sucrose, ovalbumin, and hydroxyethyl cellulose.

In preparing one or more microarrays, a coatable composition is applied to the microneedles using any of a variety of coating methods. In some embodiments, the placement of coatable composition is targeted for those portions of the microneedles that are most likely to penetrate the skin, such as on the distal portions or tips of the microneedles which comprise the distal half to distal one third of a microneedle. For example, the coatable composition can be coated onto the microneedles of a microarray by immersion, spray coating and/or roll coating, dip-coating or the like. On suitable roll coating method for use in the present invention is that disclosed in U.S. patent application Ser. No. 10/099,604, filed Mar. 15, 2002.

Following placement, the coatable composition is dried to provide a coating comprising the active agent and biological salt. Those skilled in the art will appreciate that the thickness of the dried coating will be dependent on the density of the microneedles on the microarray and the viscosity and concentration of the coating composition as well as the coating method chosen. In some embodiments, the coatable composition will be applied to a microarray to achieve a dried coating thickness of less than about 100 microns. In some embodiment, the dried coating thickness is less than 50 microns. In other embodiments, the dried coating thickness is less than 10 microns. In still other embodiments, the dried coating thickness is in the range of about 1 to about 10 microns.

Following the application of a coatable composition, it can be dried to remove volatile components, such as solvents and the like, to provide a dried coating comprising active agent and biological salt. As used herein, the term "dried coating" refers to a coating that is substantially free of volatile solvent, but the dried coatings may retain some moisture, typically in equilibrium with the atmosphere surrounding the microneedle array. In embodiments of the invention, the composition is dried at ambient temperature, with or without a forced air current. In other embodiments, the coatable composition is dried by the application of heat in an oven or the like. Alternatively, the coated composition can be lyophilized, freeze dried, air dried, vacuum dried or the like in order to remove solvent and other volatile components and provide a dried coating. Drying or evaporation conditions may be selected so as to avoid degradation of the active agent and the biological salt in the dried coating.

Figure 2:
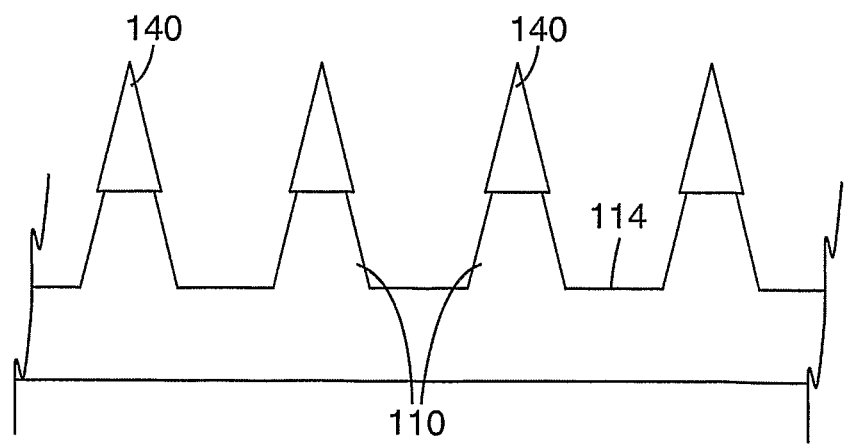
FIG. 2 is a side elevation, in cross section, of a portion of a microarray having a plurality of microneedles, the distal ends of each microneedle coated with a composition comprising an active agent, according to the invention.

Referring to FIG. 2, a portion of a microarray is illustrated with a dried coating 140 comprising an active agent disposed on the distal portion or tip of each microneedle 110. In some embodiments, the distal portion of a microneedle can comprise the distal-most one half portion of the surface area of a microneedle. In other embodiments, the distal portion of a microneedle can comprise the distal-most one third of the surface of the microneedle. In still other embodiments, the distal portion of a microneedle can comprise a portion of a microneedle's surface area that is less than the distal-most one third thereof. The dried coating 140 may be in the form of any of a variety of shapes such as a thin laminar coating, like that shown in FIG. 2, disposed over the distal portions or tips of the microneedles 110. In some embodiments, the dried coating may be more rounded in its configuration so that it resembles a droplet disposed on the tips of the microneedles 110. The dried coating may be uniformly configured across a microneedle so that the coating is symmetrical and more or less adapts the same shape as that of the microneedle. However, the shape of the dried coating may also vary so that it is asymmetrical over any single microneedle or it may vary in appearance and configuration from one microneedle to the next in a microarray. It will also be appreciated that the dried coating may at least partially extend to the lower portions of the microneedles 110 nearest the surface of support substrate 114. In some embodiments, the dried coating may also be deposited on at last a portion of the substrate 114.

Microarray devices may also be used for immediate delivery, that is where they are applied and immediately removed from the application site. They may also be left in place for an extended time, which may range from a few minutes to as long as 1 week. It will be appreciated that the microarray devices may be provided in the form of a "patch" that can be adhered to the skin during the time needed to deliver active agent through the stratum corneum. In some embodiments of the invention, a microarray having a dried coating as described herein may be applied to mammalian skin for an extended time of delivery such as from about 1 to about 30 minutes to allow for more complete vaccination than can be obtained upon application and immediate removal. In another aspect, an extended time of delivery may be as long as 1 hour, 1 day, or 1 week.

Preparative and Test Procedures

In the Examples that follow, certain procedures were followed in the preparation of the Examples and in carrying out the testing described herein.

Testing Procedure for Tetanus Toxoid Total-Array Content

A sample extraction solvent was prepared containing 50 mM potassium perchlorate, 50 mM potassium citrate, 20 mM sodium phosphate, 376 mM sodium chloride, and 100 μg/mL bovine serum albumin. A high performance liquid chromatography ("HPLC") sample solution was prepared by placing an array into a polypropylene cup, adding 1.0 mL of the sample extraction solvent to the cup, snapping a cap onto the sample cup, and sonicating for 30 minutes.

Gradient elution HPLC (Mobile phase A): 0.2% (v/v) perchloric acid; Mobile phase B: 10% water, 88% acetonitrile, 2% isopropanol, 0.2% perchloric acid (70%); Solvent Program: 0.00 min, 22% B, 1.0 mL/min; 6.00 min, 58% B, 1.0 mL/min; 6.01 min, 100% B, 1.0 mL/min; 6.50 min, 100% B, 0.5 mL/min; 10.0 min, 0% B, 0.5 mL/min; Injection Volume: 100 uL; Column: Zorbax 300SB-C8 50×4.6 mm, 3.5 micron) was used to quantify tetanus toxoid in the HPLC sample solution.

Non-adjuvanted tetanus toxoid (TT) vaccine (Aventis) was calibrated against a lyophilized TT primary standard (List Biologics) and used as a working standard. The working standard was used to obtain a calibration curve from approximately 1 ug-TT/mL to 28 ug-TT/mL. The correlation coefficient for the linear regression of the calibration curve was typically greater than 0.999. Tetanus toxoid content results are the average of between 6 and 10 replicates.

Testing Procedure for Tetanus Toxoid Tip-Content

Tetanus toxoid content on the tips of the microneedles was measured by fixing the toxoid in place on the substrate and lower portions of the microneedles so that it could not be extracted into the HPLC sample solution. A microneedle array was placed on a flat surface with the needles pointing upward and 10 μL of an oil-based polyurethane coating solution (MINWAX Fast-Drying Polyurethane) was applied to the array and allowed to coat the substrate of the array. The polyurethane was allowed to cure for at least 3 hours at ambient conditions. The array was subsequently extracted and analyzed as described in the total content method.

Aluminum Content by Inductively Coupled Plasma (ICP)

A 0.5 mL aliquot of the HPLC sample solution (described above) was diluted to 5.0 mL with 4% nitric acid for analysis of aluminum by ICP. The analysis was calibrated by using aluminum standards at 1, 2, 4, 5, 6, 8 and 11 μg/mL. The correlation coefficient for the linear regression of the calibration curve was typically greater than 0.999.

Enzyme-Linked Immunosorbant Assay (ELISA)

Quantitative determination of anti-tetanus toxoid IgG from rabbit serum was performed by ELISA. Tetanus toxoid is coated on the solid phase and binds anti-tetanus toxoid IgG from rabbit serum samples. Plates are washed and bound rabbit IgG is detected with an anti-rabbit IgG-HRP conjugate. The assay was standardized against the EP veterinary standard rabbit anti-tetanus toxoid BRP Batch 1 (EDQM-European Pharmacopoeia Commission catalog number C2425600). 1000 arbitrary units (AU) from this ELISA is equivalent to 1 international unit (IU). Unless otherwise noted, anti-tetanus toxoid IgG results are reported as the geometric average of 5 replicates.

Preparation of Microneedle Arrays

Microneedle arrays were prepared as follows. A circular disk (area 2 $cm^2$, thickness 1.02 mm) that was partially patterned with an array of microneedles (37×37) in a square shape (1 $cm^2$) centered on one side of the disk was prepared.

The needles were regularly spaced with a distance of 275 microns between the tips of adjacent needles in a square-shaped pattern. Individual needles were pyramidal in shape with a height of 250 microns and a square base having a side-length of 83.3 microns. The tips were truncated with a flat, square-shaped top having a side-length of 5 microns. Arrays were injection molded according to the general description provided in International Patent Application Publication No. WO 05/82596 and made from polycarbonate (LEXAN HPS1R-1125, GE Plastics, Pittsfield, Mass.). The center of the disk was then die cut to provide a microneedle array (area=1 cm$^2$) having microneedles on approximately 90% of the surface of the patterned side of the disk. The microneedle array had approximately 1200 microneedles.

EXAMPLES

Additional features of the embodiments of the invention are illustrated in the following non-limiting Examples.

Example 1

A polyvinylpyrrolidone (PVP) stock solution was prepared by adding 825 mg PVP (PLASDONE K-29/32, Povidone USP, ISP Technologies, Wayne, N.J.) to 25 mL water and mixing until the PVP was dissolved. A stock solution was prepared by adding 50 mg polysorbate 80 (TWEEN-80, Sigma Chemical Co., St. Louis, Mo.) to 25 mL ethanol. A diluted stock solution was prepared by adding 2 mL of the polysorbate stock solution to 18 mL ethanol. A PVP priming solution was prepared by adding 1 mL of the PVP stock solution to 9 mL of the diluted polysorbate stock solution. A microneedle array was placed on a flat surface with the needles pointing upward and an aliquot of 30 µL of the PVP priming solution was applied to the center of the array using a pipette and allowed to spread across the array. The PVP priming solution was allowed to dry at ambient conditions.

TWEEN-80 (90 mg) was added to water (30 mL) to prepare a TWEEN-80 stock solution with a concentration of 3 mg/mL. PVP (1.8 g) was added to water (20 mL) to prepare a PVP stock solution with a concentration of 90 mg/mL. Sucrose (1.8 g) was added to water (20 mL) to prepare a sucrose stock solution with a concentration of 90 mg/mL. Potassium citrate (1.8 g) was added to water (20 mL) to prepare a potassium citrate stock solution with a concentration of 90 mg/mL. An antigen coating formulation was prepared by mixing tetanus toxoid (Statens Serum Institute Lot 92-1, 888 Lf/mL) with aliquots of the TWEEN-80, PVP, sucrose and potassium citrate stock solutions.

An aliquot (15 μL) of masking fluid (FC-43 FLUORINERT Electronic Liquid) was applied to the center of the array using a pipette and allowed to spread across the array. A 10 μL aliquot of the antigen coating formulation was applied to the center of the masking fluid on the array using a pipette. The nominal amount of tetanus toxoid in the applied antigen coating formulation was 10 μg. The nominal amount of TWEEN-80 in the applied antigen coating formulation was 6 μg. The nominal amounts of PVP, sucrose, and potassium citrate were 100 μg. The antigen coating formulation and masking fluid were allowed to dry at ambient conditions for approximately 30 minutes to provide a dried antigen coating on the array. Tetanus toxoid total-array content as measured by reversed phase HPLC was 11.9 μg (st. dev.=0.5 μg). Tetanus toxoid tip-content was measured as 5.0 μg (st. dev.=1.2 μg).

Examples 2-5

Coated arrays were prepared according to the procedure described in Example 1 with the exception that the nominal amounts of PVP, sucrose and potassium citrate were varied, as shown in Table 1. Tetanus toxoid content of the coated array as measured by reversed phase HPLC and tetanus toxoid content on the tips of the microneedles was measured. The results are shown in Table 1.

TABLE 1

| | | | | Tetanus toxoid content | |
|---|---|---|---|---|---|
| Ex. No. | PVP [μg] | Sucrose [μg] | Potassium citrate [μg] | Total-array, Mean(st. dev) [μg] | Tip-content, Mean(st. dev) [μg] |
| 1 | 100 | 100 | 100 | 11.9 (0.5) | 5.0 (1.2) |
| 2 | 100 | 100 | 10 | 13.1 (0.4) | 8.5 (0.5) |
| 3 | 10 | 10 | 100 | 11.6 (0.8) | 9.3 (1.3) |
| 4 | 10 | 100 | 10 | 11.5 (0.3) | 9.1 (1.4) |
| 5 | 100 | 10 | 10 | 12.3 (0.3) | 6.9 (0.7) |

In Vivo Tetanus Toxoid Deposition

Microneedle devices were prepared by adhering antigen coated arrays as described in Examples 1 to 5 to an adhesive backing. The arrays were applied to hairless guinea pigs using an applicator as generally described in U.S. Patent Application Ser. No. 60/578,651, the disclosure of which is hereby incorporated by reference. The applicator piston mass was 5.08 g and the devices were applied at a velocity of 8.07 meters/second. The devices were applied to sites on the soft tissue of the abdomen and muscle on the lower back below the ribs and just above the pelvis. The application sites were cleaned with 70% isopropyl alcohol and allowed to air dry for at least 30 seconds prior to device application. Devices (N=5) were removed at specified time points and the tetanus toxoid content remaining on the arrays was measured by HPLC. The results are summarized in Table 2.

TABLE 2

| | tetanus toxoid content [μg] | | | | |
|---|---|---|---|---|---|
| Array Example No. | T = 0 min | T = 1 min | T = 5 min | T = 10 min | T = 20 min |
| 1 | 11.9 | 9.8 | 10.3 | 8.6 | 8.1 |
| 2 | 13.1 | 10.9 | 10.1 | 8.2 | 8.1 |
| 3 | 11.6 | 9.1 | 8.1 | 7.6 | 6.3 |
| 4 | 11.5 | 9.9 | 8.6 | 8.2 | 7.0 |
| 5 | 12.3 | 11.1 | 9.8 | 10.0 | 8.5 |

Example 6

A polyvinyl alcohol priming solution was prepared as follows. An amount (250 mg) of polyvinyl alcohol (80% hydrolyzed, typical Mw=9,000-10,000, CAS 9002-89-5, Aldrich, St. Louis, Mo.) was added to water (25 mL) to prepare a polyvinyl alcohol stock solution. An aliquot of polyvinyl alcohol stock solution (2 mL) was added to ethanol (18 mL) to prepare a polyvinyl alcohol priming solution. A microneedle array was placed on a flat surface with the needles pointing upward and an aliquot of 30 μL of the polyvinyl alcohol priming solution was applied to the center of the array using a pipette and allowed to spread across the array. The polyvinyl alcohol priming solution was allowed to dry at ambient conditions. An aliquot (15 µL) of masking fluid (FC-43 FLUORINERT Electronic Liquid) was then applied to the center of the array using a pipette and allowed to spread across the array. A 10 µL aliquot of the antigen coating formulation was applied to the center of the masking fluid on the array using a pipette. Antigen coating formulations were prepared according to the general procedure described in Example 1. The nominal amount of tetanus toxoid in the applied antigen coating formulation was 10 µg. The nominal amount of TWEEN-80 in the applied antigen coating formulation was 6 µg. The nominal amounts of PVP, sucrose, and potassium citrate were 100 µg. The antigen coating formulation and masking fluid were allowed to dry at ambient conditions for approximately 30 minutes to provide a dried antigen coating on the array. Tetanus toxoid total-array content as measured by reversed phase HPLC was 10.4 µg (st. dev.=0.7 µg). Tetanus toxoid tip-content was measured as 9.3 µg (st. dev.=0.4 µg).

Examples 7-14

Coated arrays were prepared according to the procedure described in Example 6 with the exception that the nominal amounts of PVP, sucrose and potassium citrate were varied, as shown in Table 3. Tetanus toxoid content of the coated array as measured by reversed phase HPLC and tetanus toxoid content on the tips of the microneedles was measured. The results are shown in Table 3.

TABLE 3

| | | | | Tetanus toxoid content | |
|---|---|---|---|---|---|
| Ex. No. | PVP [µg] | Sucrose [µg] | Potassium citrate [µg] | Total-array, Mean (st. dev) [µg] | Tip-content, Mean (st. dev) [µg] |
| 6 | 100 | 100 | 100 | 10.4 (0.7) | 9.3 (0.4) |
| 7 | 100 | 100 | 10 | 10.4 (0.3) | 8.2 (0.8) |
| 8 | 100 | 10 | 100 | 10.2 (0.6) | 9.1 (0.3) |
| 9 | 10 | 100 | 100 | 9.5 (0.9) | 6.7 (1.0) |
| 10 | 10 | 10 | 100 | 9.3 (0.4) | 5.8 (1.1) |
| 11 | 10 | 100 | 10 | 9.5 (0.5) | 6.9 (0.9) |
| 12 | 100 | 10 | 10 | 10.2 (0.4) | 5.6 (1.4) |
| 13 | 10 | 10 | 10 | 7.9 (0.2) | 4.5 (0.7) |
| 14 | 55 | 55 | 55 | 10.6 (0.4) | 8.4 (0.5) |

Example 15

A coated array was prepared according to the procedure described in Example 7. Tetanus toxoid total-array content as measured by reversed phase HPLC was 10.7 µg (st. dev.=0.9 µg). Tetanus toxoid tip-content was measured as 8.7 µg (st. dev.=0.6 µg). Arrays were applied to hairless guinea pigs as described above in the section "in vivo tetanus toxoid deposition". The amount of tetanus toxoid remaining on the array after removal from the hairless guinea pig was measured by HPLC. The results are summarized in Table 4.

Example 16

A coated array was prepared according to the procedure described in Example 8. Tetanus toxoid total-array content as measured by reversed phase HPLC was 11.4 µg (st. dev.=0.3 µg). Tetanus toxoid tip-content was measured as 8.6 µg (st. dev.=0.5 µg). Arrays were applied to hairless guinea pigs as described above in the section "in vivo tetanus toxoid deposition". The amount of tetanus toxoid remaining on the array after removal from the hairless guinea pig was measured by HPLC. The results are summarized in Table 4.

Example 17

A coated array was prepared according to the procedure described in Example 9. Tetanus toxoid total-array content as measured by reversed phase HPLC was 10.8 µg (st. dev.=0.3 µg). Tetanus toxoid tip-content was measured as 6.8 µg (st. dev.=0.9 µg). Arrays were applied to hairless guinea pigs as described above in the section "in vivo tetanus toxoid deposition". The amount of tetanus toxoid remaining on the array after removal from the hairless guinea pig was measured by HPLC. The results are summarized in Table 4.

Example 18

A coated array was prepared according to the procedure described in Example 13. Tetanus toxoid total-array content as measured by reversed phase HPLC was 11.7 µg (st. dev.=0.3 µg). Tetanus toxoid tip-content was measured as 5.3 µg (st. dev.=1.0 µg). Arrays were applied to hairless guinea pigs as described above in the section "in vivo tetanus toxoid deposition". The amount of tetanus toxoid remaining on the array after removal from the hairless guinea pig was measured by HPLC. The results are summarized in Table 4.

TABLE 4

| | tetanus toxoid content [µg] | | | | |
|---|---|---|---|---|---|
| Array Example No. | T = 0 min | T = 1 min | T = 5 min | T = 10 min | T = 20 min |
| 15 | 10.7 | 10.6 | 8.8 | 7.8 | 6.3 |
| 16 | 11.4 | 10.2 | 8.4 | 8.1 | 7.3 |
| 17 | 10.8 | 9.3 | 9.2 | 8.4 | 7.5 |
| 18 | 11.7 | 9.7 | 9.7 | 8.3 | 7.9 |

Example 19

Microneedle arrays were prepared as described above and treated as follows. The arrays were plasma treated using a Plasma-Therm VII 7000 series plasma processing system. A diamond-like glass thin film was formed through plasma deposition by feeding a mixture of tetramethyl silane (150 standard cubic centimeter per minute, sccm) and oxygen (200 sccm) gas in an unpressurized plasma with 2000 W RF power applied for 15 seconds. The arrays were then subsequently treated with an oxygen plasma (400 sccm) under a pressure of 150 mTorr with 300 W power for 60 seconds to remove elemental and covalently bonded carbon from the surface atomic layers and to make the surface hydrophilic.

An aliquot (15 µL) of masking fluid (FC-43 FLUORINERT Electronic Liquid) was applied to the center of the array using a pipette and allowed to spread across the array. A 10 µL aliquot of the antigen coating formulation was applied to the center of the masking fluid on the array using a pipette. Antigen coating formulations were prepared according to the general procedure described in Example 1. The nominal amount of tetanus toxoid in the applied antigen coating formulation was 10 µg. The nominal amount of TWEEN-80 in the applied antigen coating formulation was 6 µg. The nominal amounts of PVP, sucrose, and potassium citrate were 100 µg. The antigen coating formulation and masking fluid were allowed to dry at ambient conditions for approximately 30 minutes to provide a dried antigen coating on the array. Tetanus toxoid total-array content as measured by reversed phase HPLC was 12.1 μg (st. dev.=0.6 μg). Tetanus toxoid tip-content was measured as 9.6 μg (st. dev.=1.2 μg). Arrays were applied to hairless guinea pigs as described above in the section "in vivo tetanus toxoid deposition". The amount of tetanus toxoid remaining on the array after removal from the hairless guinea pig was measured by HPLC. The results are summarized in Table 6.

Examples 22-23

Coated arrays were prepared according to the procedure described in Example 19 with the exception that the nominal amounts of PVP, sucrose and potassium citrate were varied, as shown in Table 5. Tetanus toxoid content of the coated array as measured by reversed phase HPLC and tetanus toxoid content on the tips of the microneedles was measured. The results are shown in Table 5. Arrays were applied to hairless guinea pigs as described above in the section "in vivo tetanus toxoid deposition". The amount of tetanus toxoid remaining on the array after removal from the hairless guinea pig was measured by HPLC. The results are summarized in Table 6.

TABLE 5

| Ex. No. | PVP [μg] | Sucrose [μg] | Potassium citrate [μg] | Tetanus toxoid content | |
|---|---|---|---|---|---|
| | | | | Total-array, Mean (st. dev) [μg] | Tip-content, Mean (st. dev) [μg] |
| 19 | 100 | 100 | 100 | 12.1 (0.6) | 9.6 (1.2) |
| 20 | 100 | 100 | 10 | 12.4 (0.4) | 9.3 (1.7) |
| 21 | 10 | 10 | 100 | 12.3 (0.4) | 8.3 (0.8) |
| 22 | 10 | 100 | 10 | 11.3 (0.4) | 8.3 (1.3) |
| 23 | 100 | 10 | 10 | 12.3 (0.3) | 8.4 (2.0) |

TABLE 6

| Array Example No. | tetanus toxoid content [μg] | | | | |
|---|---|---|---|---|---|
| | T = 0 min | T = 1 min | T = 5 min | T = 10 min | T = 20 min |
| 19 | 12.1 | 9.6 | 9.7 | 8.0 | 8.4 |
| 20 | 12.4 | 10.5 | 9.8 | 8.4 | 7.9 |
| 21 | 12.3 | 10.7 | 10.4 | 10.1 | 10.2 |
| 22 | 11.3 | 8.4 | 9.1 | 8.3 | 7.6 |
| 23 | 12.3 | 10.4 | 9.5 | 7.7 | 8.2 |

Embodiments of the invention have been described in detail. Those skilled in the art will appreciate that changes and modifications may be made to the described embodiments without departing from the true scope and spirit of the invention.

What is claimed:

1. A microarray comprising:
   a plurality of microneedles extending from a support substrate; and
   a coating deposited on at least one of the plurality of microneedles, the coating comprising an active agent and a biological salt, wherein the coating is obtainable from a coatable composition comprising 100 parts by weight of at least one active agent and at least 50 parts by weight of at least one biological salt.

2. A microarray according to claim 1 wherein the height of the microneedles is between about 1 μm and about 400 μm.

3. A microarray according to claim 1 wherein the microneedles each have an aspect ratio of at least about 2:1.

4. A microarray according to claim 1 wherein the microneedles each have an aspect ratio of at least about 3:1.

5. A microarray according to claim 1 wherein the microneedles each have an aspect ratio of at least about 5:1.

6. A microarray according to claim 1 wherein the microarray comprises up to 1000 microneedles extending from a support substrate.

7. A microarray according to claim 1 wherein each microneedle comprises a base portion attached to the support substrate and a tip portion distal from the support substrate, the coating being on the tip portion of at least one of the plurality of microneedles.

8. A microarray according to claim 1 wherein the biological salt is selected from monosodium citrate, disodium citrate, trisodium citrate, monopotassium citrate, dipotassium citrate, tripotassium citrate, and combinations of two or more of the foregoing.

* * * * *

UNITED STATES PATENT AND TRADEMARK OFFICE
CERTIFICATE OF CORRECTION

PATENT NO.      : 8,900,180 B2
APPLICATION NO. : 12/092733
DATED           : December 2, 2014
INVENTOR(S)     : James Wolter It is certified that error appears in the above-identified patent and that said Letters Patent is hereby corrected as shown below:

SPECIFICATION

Column 1
Line 10, Delete "PCT/US2005/041585," and insert -- PCT/US2005/041858, --, therefor.

Column 3
Line 3-4, Delete "polysaccarides," and insert -- polysaccharides, --, therefor.

Line 4, Delete "oligosaccarides," and insert -- oligosaccharides, --, therefor.

Line 55, Delete "form" and insert -- from --, therefor.

Column 4
Line 41, After "2003" insert -- (Atty. Ref. 57901US005) --.

Column 5
Line 15, After "2004" insert -- (Attorney Ref. 60350US002) --.

Column 6
Line 37, Delete "Papiloma" and insert -- papilloma --, therefor.

Line 41-42, Delete "filamenteous" and insert -- filamentous --, therefor.

Line 46, Delete "bronchiollitis" and insert -- bronchiolitis, --, therefor.

Column 7
Line 3, Delete "Norcardia)," and insert -- Nocardia), --, therefor.

Line 5, Delete "anthrasis)," and insert -- anthracis), --, therefor.

Signed and Sealed this
Twenty-sixth Day of May, 2015

Michelle K. Lee
*Director of the United States Patent and Trademark Office*

Line 7, Delete "Candidia," and insert -- Candida, --, therefor.

Line 9, Delete "dificile," and insert -- difficile, --, therefor.

Line 11, Delete "diptheriae)," and insert -- diphtheria), --, therefor.

Line 11, Delete "Dennatocycoses," and insert -- Dermatomycosis, --, therefor.

Line 22, Delete "Pasteurellacea," and insert -- Pasteurellaceae, --, therefor.

Line 26, Delete "Meningiococcus," and insert -- Meningococcus, --, therefor.

Line 49, Delete "dermatocycoses)," and insert -- dermatomycosis), --, therefor.

Line 50, Delete "noscomial" and insert -- nosocomial --, therefor.

Line 56, Delete "Giardias," and insert -- Giardiasis, --, therefor.

Line 56, Delete "Schistisoma," and insert -- Schistosoma, --, therefor.

Line 56-57, Delete "Theileriasis," and insert -- Theileriosis, --, therefor.

Line 58, Delete "virax," and insert -- vivax, --, therefor.

Line 58-59, Delete "falciparium," and insert -- falciparum, --, therefor.

Column 8
Line 29, Delete "amd" and insert -- and --, therefor.

Column 10
Line 50, Delete "Immunosorbant" and insert -- Immunosorbent --, therefor.

Column 14
Line 58, Delete "pipette," and insert -- pipette. --, therefor.